(12) United States Patent
van Aar et al.

(10) Patent No.: US 7,030,241 B2
(45) Date of Patent: Apr. 18, 2006

(54) MESYLATES OF PIPERAZINE DERIVATIVES AND PROCESS FOR THEIR PREPARATION

(75) Inventors: Marcel P. M. van Aar, Weesp (NL); Stefanus J. Schouten, Weesp (NL); Jan Zorgdrager, Weesp (NL); Michiel C. Heslinga, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 341 days.

(21) Appl. No.: 10/468,098

(22) PCT Filed: Feb. 14, 2002

(86) PCT No.: PCT/EP02/01666

§ 371 (c)(1),
(2), (4) Date: Aug. 15, 2003

(87) PCT Pub. No.: WO02/066449

PCT Pub. Date: Aug. 29, 2002

(65) Prior Publication Data

US 2004/0077631 A1    Apr. 22, 2004

(30) Foreign Application Priority Data

Feb. 16, 2001   (EP) ................... 01200534

(51) Int. Cl.
  *C07D 403/00*   (2006.01)
  *C07D 401/00*   (2006.01)
  *C07D 405/00*   (2006.01)
  *C07D 409/00*   (2006.01)

(52) U.S. Cl. ............. 544/359; 544/363; 544/373; 544/376

(58) Field of Classification Search ............. 544/359, 544/363, 373, 376
See application file for complete search history.

(56) References Cited

U.S. PATENT DOCUMENTS

| 4,782,061 A | 11/1988 | Kruse et al. ............... 514/254 |
| 2005/0107396 A1 | 5/2005 | Eijgendaal et al. |

FOREIGN PATENT DOCUMENTS

| EP | 0 189 612 | | 8/1986 |
| JP | 4-26683 | * | 1/1992 |
| WO | WO 97/36893 | | 10/1997 |
| WO | WO 99/05134 | | 2/1999 |
| WO | WO 00/29397 | | 5/2000 |

* cited by examiner

*Primary Examiner*—James O. Wilson
*Assistant Examiner*—Zachary C. Tucker
(74) *Attorney, Agent, or Firm*—Finnegan, Henderson, Farabow, Garrett & Dunner, L.L.P.

(57) ABSTRACT

The invention relates to the mesylates of a group of piperazine derivatives and to a process for the preparation of these mesylates in an economic way in the high yield and of high purity. According to the process of the invention the synthesis of the piperazine ring and the mesylate formation are combined in a single reaction step. The invention relates to the mesylate of compounds of the formula (I) wherein X is a bicyclic heterocyclic phenyl group and Y is methyl, ethyl (optionally substituted with fluorine), cycloalkyl (3–7C) methyl, benzyl or m-phenyl benzyl

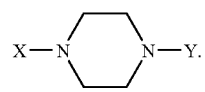

(I)

13 Claims, No Drawings

MESYLATES OF PIPERAZINE DERIVATIVES AND PROCESS FOR THEIR PREPARATION

This application is a National Stage application under 35 U.S.C. § 371 of PCT/EP/02/01666, filed Feb. 14, 2002, which claims priority from application EP 01200534.4, filed Feb. 16, 2001.

The present invention relates to a new process for the preparation of mesylates of piperazine derivatives.

It is described in Japanese patent No. 3,044,383 that piperazine derivatives can be obtained by reaction of a primary amine with a reactive ester of a substituted di(hydroxyethyl)amine. This reactive ester derivative is obtained by reacting the substituted di(hydroxyethyl)amine compound with a sulfonylhalide of the general formula $R^1SO_2$-Hal, wherein $R^1$ represents alkyl or aryl, and Hal is a halogen atom. Using this process hydrochloric or hydrobromic acid addition salts of the desired piperazine derivatives are obtained. To obtain the corresponding mesylate the obtained salt has to be converted into the free base, from which the desired mesylate can be prepared by using methane sulfonic acid.

It has now been found that the mesylates of such piperazine derivatives can be obtained directly in an economic way in high yield and high purity according to the process of the invention.

The present invention relates to a novel process for the preparation of the mesylate of compounds having the formula (1)

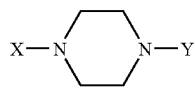

(1)

by reacting an amine of the formula (2)

X—NH₂ (2)

with a compound of the formula (3)

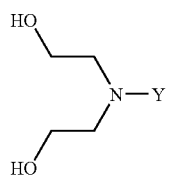

(3)

and methanesulfonic anhydride, in which formulae X represents a group of the formula (4)

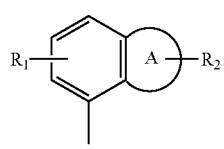

(4)

wherein
R₁ is hydrogen or fluoro
R₂ is hydrogen, alkyl (1–4 C), alkoxy (1–4 C) or an oxo group,
A represents a heterocyclic group of 5–7 ring atoms wherein 1–3 heteroatoms from the group O, N and S are present,
Y is methyl, ethyl, ethyl substituted with one or more fluorine atoms, cycloalkyl (3–7 C) methyl optionally substituted with one or more fluorine atoms, or a group of the formula (5)

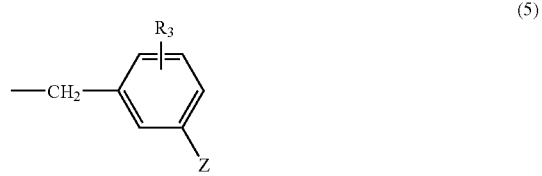

(5)

wherein Z is hydrogen, phenyl, phenyl substituted with 1–3 substituents from the group hydroxy, halogen, alkyl (1–4 C), alkoxy (1–4 C) or cyano, and R₃ is hydrogen or 1–3 substituents from the group halogen, hydroxy, alkyl (1–4 C) or alkoxy (1–4 C).

Preferably the invention relates to the preparation of mesylates of compounds having formula (1) wherein X is the group having formula (6)

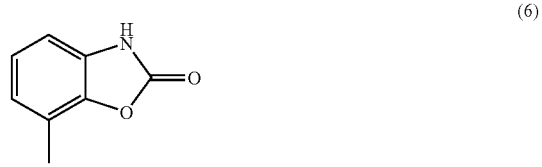

(6)

and Y has the above meanings.

Especially the invention relates to the preparation of mesylates of compounds having formula (1) wherein X is the group having formula (6), and Y represents m-phenyl benzyl, benzyl or methyl.

According to the process of the invention the synthesis of the piperazine ring and the mesylate formation are combined in one single step which is of great advantage.

The formation of the reactive ester of a compound having formula (3) by reacting it with methanesulfonic anhydride is preferably carried out in the presence of a base such as triethyl amine. This reaction can be carried in an organic solvent at temperatures between 0 and 150° C., preferably at reflux temperature.

Suitable solvents are for example mono chlorobenzene and methyl ethyl ketone. The starting compounds having formula (2) and (3) are either known compounds, or can be prepared in the same manner as structurally related known compounds.

The mesylates of the compounds having formula (1) are novel compounds. A number of free bases, hydrochloric acid addition salts and fumarates of such compound are known already.

The invention also relates to the novel mesylates of the compounds having formula (1).

The invention especially relates to mesylates of compounds having formula (1) wherein X is the group of the formula (6)

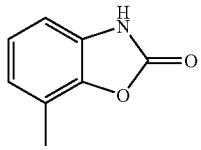

(6)

and Y has the above meanings.

More especially the invention relates to mesylates of compounds having formula (1) wherein X is the group having formula (6) and Y represents m-phenylbenzyl, benzyl or methyl.

The invention particularly relates to the mesylates of the compound having formula (1) wherein X is the group having formula (6) and Y represents the group m-phenyl benzyl.

The hydrochloric acid addition salt of the compounds having formula (1), together with its interesting pharmacological properties are known from WO 97/36893. A disadvantage of this known HCl-salt is the poor solubility thereof in water. At 25° C. the solubility after 2, 4, 8 and 24 hours respectively is between 0.18 and 0.20 mg/ml.

It has now been found that the mesylate of this compound is about 8–10 times better soluble in water, i.e. 1.7 mg/ml at 25° C. This higher solubility is of great importance since it results in a better bioavailability of the active compound. The invention is illustrated in the following example.

EXAMPLE

A solution of 27.14 g (100 mmol) of di(hydroxyethyl) m-phenyl benzyl amine in 150 ml of methyl ethyl ketone (MEK) is charged under nitrogen into a 1000 ml round bottomed flask equipped with a thermometer, reflux condensor and mechanical stirrer. An amount of 42.50 g (240 mmol) of methanesulfonic anhydride is dissolved at room temperature while stirring. The reaction mixture is cooled to 0–5° C., and 44.77 g (440 mmol) of triethylamine in 50 ml of MEK is added dropwise in 30–45 min. keeping the temperature below 10° C. Another 40 ml of MEK is added while stirring for 15 min. at 0–5° C. In 10–25 min. 23.08 g (240 mmol) of methanesulfonic acid in 30 ml of MEK is added dropwise while maintaining the temperature below 10° C. After rinsing with 30 ml of MEK while stirring for 15 min. cooling is stopped, and 15.01 g (100 mmol) of the compound having formula (2) wherein X is the group of formula (6) is added. The mixture is rinsed with 130 ml of MEK, and warmed at 20–25° C. for 1 hour. The clear solution is filtered into another flask and washed with 60 ml. of MEK. The mixture is heated till reflux and about 60 ml of MEK is distilled off. Reflux is continued for 8–24 hours and 140 ml of MEK are added. Then 150 ml of water/MEK are distilled off and the mixture is cooled to 0–5° C. and stirred at this temperature for another 2 hours. The product, i.e. the desired mesylate, is filtered, washed twice with 75 ml of cold MEK (0–5° C.), and dried at 50° (100 mbar) under nitrogen. Yield 33.3 g; melting range 263–275° C.

In a similar manner the mesylates of the compounds having formula 1 wherein

1) X is the group of formula (6) and Y is benzyl
2) X is the group of formula (6) and Y is methyl have been prepared.

The invention claimed is:

1. A methane sulfonic acid salt of a compound of formula (1)

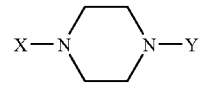

(1)

wherein:

X is a group of formula (4)

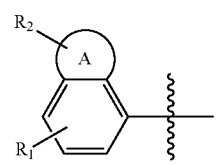

(4)

wherein A is a heterocyclic group having from 5 to 7 ring atoms, wherein the ring atoms comprise from 1–3 heteroatoms independently chosen from O, N, and S; $R_1$ is chosen from hydrogen and fluoro; and $R_2$ is chosen from hydrogen, $C_{1-4}$ alkyl, $C_{1-4}$ alkoxy, and an oxo group;

Y is chosen from methyl, ethyl, ethyl substituted with at least one fluorine atom, $C_{3-7}$ cycloalkyl methyl which is optionally substituted with at least one fluorine atom, and a group of formula (5)

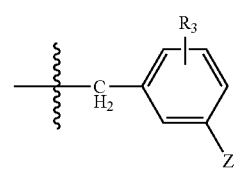

(5)

wherein Z is chosen from hydrogen; phenyl; phenyl substituted with 1–3 substituents independently chosen from hydroxy, $C_{1-4}$ alkyl, $C_{1-4}$ alkoxy, and cyano; and $R_3$ is chosen from hydrogen or 1–3 substituents independently chosen from halogen, hydroxy, $C_{1-4}$ alkyl, and $C_{1-4}$ alkoxy.

2. A compound according to claim 1, wherein X is

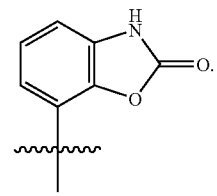

3. A compound according to claim 2, wherein Y is chosen from meta-phenylbenzyl, benzyl, and methyl.

4. A compound according to claim 3, wherein Y is meta-phenylbenzyl.

5. A compound according to claim 3, wherein Y is benzyl.

6. A compound according to claim 3, wherein Y is methyl.

7. A process of preparing a methane sulfonic acid salt of a compound of formula (1):

(1)

wherein:

X is a group of formula (4)

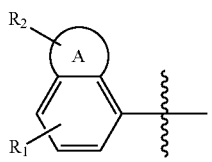
(4)

wherein A is a heterocyclic group having from 5 to 7 ring atoms, wherein the ring atoms comprise from 1–3 heteroatoms independently chosen from O, N, and S; $R_1$ is chosen from hydrogen and fluoro; and $R_2$ is chosen from hydrogen, $C_{1-4}$ alkyl, $C_{1-4}$ alkoxy, and an oxo group;

Y is chosen from methyl, ethyl, ethyl substituted with at least one fluorine atom, $C_{3-7}$ cycloalkyl methyl which is optionally substituted with at least one fluorine atom, and a group of formula (5)

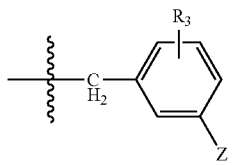
(5)

wherein Z is chosen from hydrogen; phenyl; phenyl substituted with 1–3 substituents independently chosen from hydroxy, $C_{1-4}$ alkyl, $C_{1-4}$ alkoxy, and cyano; and $R_3$ is chosen from hydrogen or 1–3 substituents independently chosen from halogen, hydroxy, $C_{1-4}$ alkyl, and $C_{1-4}$ alkoxy, said process comprising:

reacting a compound of formula

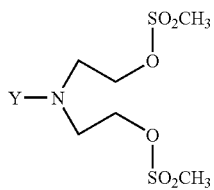

with a compound of formula (2),

X—NH$_2$ (2)

wherein X and Y are as defined above.

8. A process of preparing a methane sulfonic acid salt of a compound of formula (1):

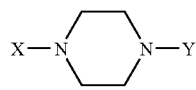
(1)

wherein:

X is a group of formula (4)

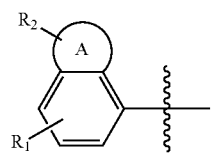
(4)

wherein A is a heterocyclic group having from 5 to 7 ring atoms, wherein the ring atoms comprise from 1–3 heteroatoms independently chosen from O, N, and S; $R_1$ is chosen from hydrogen and fluoro; and $R_2$ is chosen from hydrogen, $C_{1-4}$ alkyl, $C_{1-4}$ alkoxy, and an oxo group; Y is chosen from methyl, ethyl, ethyl substituted with at least one fluorine atom, $C_{3-7}$ cycloalkyl methyl which is optionally substituted with at least one fluorine atom, and a group of formula (5)

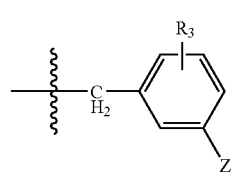
(5)

wherein Z is chosen from hydrogen; phenyl; phenyl substituted with 1–3 substituents independently chosen from hydroxy, $C_{1-4}$ alkyl, $C_{1-4}$ alkoxy, and cyano; and $R_3$ is chosen from hydrogen or 1–3 substituents independently chosen from halogen, hydroxy, $C_{1-4}$ alkyl, and $C_{1-4}$ alkoxy, said process comprising:

a) reacting a compound of formula (3),

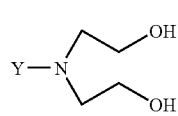
(3)

with methanesulfonic anhydride to afford a first product; and b) reacting said first product with a compound of formula (2),

X—NH$_2$ (2)

wherein Y and X are as defined above.

9. A process according to claim 8, wherein X is
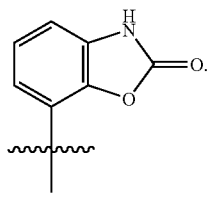
10. A process according to claim 9, wherein Y is chosen from meta-phenylbenzyl, benzyl, and methyl.
11. A process according to claim 10, wherein Y is meta-phenylbenzyl.
12. A process according to claim 10, wherein Y is benzyl.
13. A process according to claim 10, wherein Y is methyl.
* * * * *

UNITED STATES PATENT AND TRADEMARK OFFICE
CERTIFICATE OF CORRECTION

| | |
|---|---|
| PATENT NO. | : 7,030,241 B2 |
| APPLICATION NO. | : 10/468098 |
| DATED | : April 18, 2006 |
| INVENTOR(S) | : van Aar et al. |

It is certified that error appears in the above-identified patent and that said Letters Patent is hereby corrected as shown below:

In claim 7, column 5, line 31, "$C_{37}$" should read --$C_{3-7}$--.

Signed and Sealed this

Twenty-seventh Day of February, 2007

JON W. DUDAS
*Director of the United States Patent and Trademark Office*